US009312713B2

(12) United States Patent
Graf et al.

(10) Patent No.: US 9,312,713 B2
(45) Date of Patent: Apr. 12, 2016

(54) HEATING A SENSITIVE LAYER OF A CHEMICAL SENSOR SUBJECT TO DETECTION OF A RECHARGE PROCESS IN AN ELECTRONIC DEVICE

(71) Applicants: Markus Graf, Zurich (CH); Moritz Lechner, Uerikon (CH)

(72) Inventors: Markus Graf, Zurich (CH); Moritz Lechner, Uerikon (CH)

(73) Assignee: Sensirion AG, Stafa (CH)

( * ) Notice: Subject to any disclaimer, the term of this patent is extended or adjusted under 35 U.S.C. 154(b) by 321 days.

(21) Appl. No.: 13/787,200

(22) Filed: Mar. 6, 2013

(65) Prior Publication Data

US 2013/0249499 A1    Sep. 26, 2013

(30) Foreign Application Priority Data

Mar. 20, 2012   (EP) ..................... 12001959

(51) Int. Cl.
*H02J 7/04* (2006.01)
*H02J 7/00* (2006.01)
*G01N 33/497* (2006.01)
*G01N 33/487* (2006.01)

(52) U.S. Cl.
CPC ........ *H02J 7/0052* (2013.01); *G01N 33/48785* (2013.01); *G01N 33/497* (2013.01)

(58) Field of Classification Search
CPC ........... H02J 7/0052; G01N 33/48785; G01N 33/497
USPC .......................................... 320/150; 219/201
See application file for complete search history.

(56) References Cited

U.S. PATENT DOCUMENTS

| 4,784,721 | A | | 11/1988 | Holmen et al. |
| 4,899,085 | A | * | 2/1990 | Kimura et al. ................ 315/116 |
| 5,345,213 | A | | 9/1994 | Semancik et al. |
| 5,406,109 | A | | 4/1995 | Whitney |
| 5,700,367 | A | * | 12/1997 | Yamada et al. ............... 205/785 |
| 5,705,745 | A | | 1/1998 | Treutler et al. |
| 5,792,938 | A | | 8/1998 | Gokhfeld |
| 5,898,101 | A | * | 4/1999 | Lyle ..................... G01N 27/124 73/23.2 |
| 5,907,765 | A | | 5/1999 | Lescouzeres et al. |
| 6,231,519 | B1 | | 5/2001 | Blants et al. |
| 6,690,569 | B1 | | 2/2004 | Mayer et al. |
| 6,697,645 | B1 | | 2/2004 | MacFarlane |
| 6,703,241 | B1 | | 3/2004 | Sunshine et al. |
| 6,858,182 | B1 | | 2/2005 | Ito et al. |

(Continued)

FOREIGN PATENT DOCUMENTS

| CH | 6911975 | 8/2000 |
| CN | 1825120 | 8/2006 |

(Continued)

OTHER PUBLICATIONS

Albrecht Schmidt et al., "How to Build Smart Appliances,?" IEEE Personal Communications, Aug. 2001, 66-71.

(Continued)

*Primary Examiner* — Yalkew Fantu
*Assistant Examiner* — Manuel Hernandez
(74) *Attorney, Agent, or Firm* — Cooper & Dunham LLP

(57) ABSTRACT

In a method for operating a portable electronic device a recharge process for recharging a rechargeable energy storage of the portable electronic device is detected. A heater is activated for heating a sensitive layer of a chemical sensor contained in the portable electronic device subject to the detection of the recharge process.

11 Claims, 3 Drawing Sheets

(56) References Cited

U.S. PATENT DOCUMENTS

| | | | |
|---|---|---|---|
| 6,912,386 | B1 | 6/2005 | Himberg et al. |
| 7,061,061 | B2 | 6/2006 | Goodman et al. |
| 7,104,110 | B2* | 9/2006 | Oishi et al. ............... 73/1.06 |
| 7,911,010 | B2 | 3/2011 | Stetter |
| 7,991,571 | B2 | 8/2011 | Laraia et al. |
| 9,170,248 | B2* | 10/2015 | Fleischer ............ G01N 27/4141 |
| 2002/0178789 | A1 | 12/2002 | Sunshine et al. |
| 2003/0172717 | A1 | 9/2003 | Kita et al. |
| 2004/0084308 | A1* | 5/2004 | Cole ............... G01N 33/0016 204/424 |
| 2005/0009195 | A1 | 1/2005 | Wang |
| 2005/0053523 | A1 | 3/2005 | Brooke |
| 2005/0160789 | A1 | 7/2005 | Freyer et al. |
| 2007/0045129 | A1* | 3/2007 | Gu ....................... G01N 33/004 205/785 |
| 2007/0241261 | A1* | 10/2007 | Wendt ........................... 250/221 |
| 2008/0128277 | A1* | 6/2008 | Fukuda ........................ 204/401 |
| 2009/0126460 | A1* | 5/2009 | Gardner et al. ............ 73/31.06 |
| 2009/0146826 | A1 | 6/2009 | Gofman et al. |
| 2009/0215439 | A1 | 8/2009 | Hamilton et al. |
| 2010/0015992 | A1 | 1/2010 | Wakefield |
| 2010/0045300 | A1 | 2/2010 | Brothier et al. |
| 2010/0060465 | A1 | 3/2010 | Stetter |
| 2010/0089122 | A1* | 4/2010 | Abdullah ............ G01N 27/122 73/25.05 |
| 2010/0300443 | A1* | 12/2010 | Becker et al. ............ 128/204.22 |
| 2011/0181421 | A1 | 7/2011 | Nabata et al. |
| 2011/0206378 | A1* | 8/2011 | Bolling et al. ................ 398/108 |
| 2011/0307208 | A1 | 12/2011 | Graf et al. |
| 2012/0050038 | A1 | 3/2012 | Stetter |
| 2012/0105084 | A1* | 5/2012 | Kittleson ..................... 324/693 |
| 2013/0192338 | A1* | 8/2013 | Mayer ............... G01N 33/4972 73/23.3 |
| 2013/0244336 | A1 | 9/2013 | Mayer et al. |
| 2013/0344609 | A1 | 12/2013 | Mayer et al. |
| 2014/0032153 | A1 | 1/2014 | Mayer et al. |
| 2014/0109648 | A1* | 4/2014 | Fleischer ............ G01N 27/4141 73/23.2 |

FOREIGN PATENT DOCUMENTS

| | | |
|---|---|---|
| CN | 201364320 | 12/2009 |
| CN | 201733362 | 2/2011 |
| EP | 1236038 | 9/2000 |
| EP | 1092962 | 4/2001 |
| EP | 2469270 | 6/2012 |
| EP | 2479892 | 7/2012 |
| EP | 2479963 | 7/2012 |
| EP | 2498481 | 9/2012 |
| EP | 2508881 | 10/2012 |
| EP | 2620768 | 7/2013 |
| EP | 2639582 | 9/2013 |
| EP | 2642289 | 9/2013 |
| GB | 2097130 | 10/1982 |
| JP | 8125726 | 5/1996 |
| JP | 2007135008 | 5/2007 |
| JP | 2007142835 | 6/2007 |
| JP | 2010187126 | 8/2010 |
| JP | 2010237130 | 10/2010 |
| KR | 100690638 | 2/2007 |
| KR | 1020050097216 | 2/2007 |
| WO | 9222813 | 12/1992 |
| WO | 01/42776 | 6/2001 |
| WO | 02/12884 | 2/2002 |
| WO | 0212284 | 2/2002 |
| WO | 0222007 A2 | 3/2002 |
| WO | 0222007 A3 | 3/2002 |
| WO | 03043356 | 5/2003 |
| WO | 2011058224 | 5/2011 |

OTHER PUBLICATIONS

Nicolas D. Lane et al., "A Survey of Mobile Phone Sensing," IEEE Communications Magazine, Sep. 2010, 140-150.

"Embedded Sensors in Mobiles to Monitor Asthma", Digital Opportunity Channel, Nov. 24, 2009.

J. Puigcorbe et al., "High Temperature Degradation of Pt/Ti Electrodes in Micro-Hotplate Gas Sensors," J. Micromech, Microeng, 13, 2003, 119-124.

Isolde Simon et al., "Micromachined Metal Oxide Gas Sensors: Opportunities to Improve Sensor Performance," Sensors and Acuators B 73 (2001), 1-26.

Martin Heule, et al., "Minaturised Arrays of Tin Oxide Gas Sensors on Single Microhotplate Substrates Fabricated by Micromolding in Capillaries", Sensors and Actuators B 93 (2003), 100-106.

Markus Fryder et al., "A Calibration Technique for an Electronic Nose", vol. 1, Jun. 25, 1995, pp. 683-686.

European Search Report No. 13003312.9, dated Nov. 18, 2013.

A. Hierlemann, "CMOS-based Chemical Sensors", Advanced Micro and Nanosystems, vol. 2, CMOS-MEMS, 335-390.

A. Loufti et al., "Odor Recognition for Intelligent Systems," IEEE Computer Society, Jan./Feb. 2008, 41-48.

A. Friedberger et al., "Micromechanical Fabrication of Robust Low-Power Metal Oxide Gas Sensors", Sensors and Acuators B 93 (2003), 345-349.

C. Hierold et al., Biometric Capacitive CMOS Fingerprint Sensor Systems—Advanced Micro and Nanosystems, vol. 2 CMOS-MEMS.

Stefano Zampolli et al., "Ultra-low-power Components for an RFTD Tag with Physical and Chemical Sensors", Microsyst Technol, 2008, 581-588.

A. Koll et al., "A Flip-Clip Packaged CMOS Chemical Microsystem for Detection of Volatile Organic Compounds", Part of the SPIE Conference on Smart Electronics and MEMS, San Diego, California, Mar. 1998, 223-232.

David J. Nagel, "Microsensor Clusters", Elsevier, Microelectronics Journal 33 (2002), 107-119.

\* cited by examiner

HEATING A SENSITIVE LAYER OF A CHEMICAL SENSOR SUBJECT TO DETECTION OF A RECHARGE PROCESS IN AN ELECTRONIC DEVICE

CROSS REFERENCE TO RELATED APPLICATIONS

This application claims the priority of European patent application 12 001 959.1, filed on Mar. 20, 2012, the disclosure of which is incorporated herein by reference in its entirety.

BACKGROUND OF THE INVENTION

The present invention relates to a portable electronic device and to a method for operating a portable electronic device.

Today's smart phones or tablet computers contain a couple of sensors such as, for example, a gyroscope or an acceleration sensor used for detecting an orientation of the device display for having the content to be displayed adapted to such orientation.

In general, chemical sensors are known for detecting an analyte in a gas or a fluid. In particular, metal-oxide sensors are chemical sensors known to be operated at elevated temperatures of a few hundred degrees Celsius. In order to achieve these temperatures in a sensitive layer of the chemical sensor a heater thermally coupled to the sensitive layer may be heated prior to and/or during taking a sensor reading. However, such metal-oxide sensors may suffer from an offset drift when the chemical sensor is not operated, i.e. when the heater of the chemical sensor is not activated for some time. Such drift may mainly result from an adsorption of water into the sensitive layer of the chemical sensor.

SUMMARY OF THE INVENTION

According to a first aspect of the invention, a portable electronic device is provided comprising a rechargeable energy storage, a chemical sensor comprising a sensitive layer and a heater for heating the sensitive layer, and a control unit for activating the heater subject to a detection of a recharge process for recharging the energy storage.

Preferred embodiments of the portable electronic device may contain one or more of the following features:
- a detector for detecting a connection of the portable electronic device to a main supply, wherein the control unit is adapted to activate the heater subject to the detector detecting a connection to the main supply;
- the sensitive layer comprises a metal-oxide material;
- the metal-oxide material comprises one or more of tin oxide, zinc oxide, titanium oxide, tungsten oxide, indium oxide and gallium oxide;
- the sensitive layer requires an operating temperature of more than 100° Celsius, wherein the chemical sensor is integrated in a sensor chip comprising a thermally insulated structure containing the heater and the sensitive layer;
- the portable electronic device is one of a mobile phone, a handheld computer, an electronic reader, a tablet computer, a game controller, a pointing device, a photo or a video camera, a computer peripheral.

According to another aspect of the present invention a method is provided for operating a portable electronic device, comprising detecting a recharge process for recharging a rechargeable energy storage of the portable electronic device, and activating a heater for heating a sensitive layer of a chemical sensor contained in the portable electronic device subject to the detection of the recharge process.

Preferred embodiments of the method may contain one or more of the following features:
- the heater is activated in response to the detection of the recharge process;
- the heater is deactivated in response to a termination of the recharge process;
- the heater is activated subject to the detection of the recharge process and subject to a period in time elapsed since the last time the heater has been activated in response to a recharge process;
- the heater is activated in response to the detection of the recharge process if the period in time elapsed since the last time the heater has been activated in response to a recharge process exceeds a first threshold;
- the heater is activated subject to the detection of the recharge process and subject to a user request for activating the heater;
- the heater is activated in response to the detection of the recharge process if a user request for activating the heater is pending;
- the heater is activated subject to the detection of the recharge process and subject to a period in time elapsed since the last time the heater has been activated for conducting a measurement;
- the heater is activated in response to the detection of the recharge process if the period in time elapsed since the last time the heater has been activated for conducting a measurement exceeds a second threshold;
- the heater is activated subject to the detection of the recharge process and subject to a signal of a sensor;
- the sensor is a humidity sensor, and the heater is activated in response to the detection of the recharge process if an integrated signal of the humidity sensor exceeds a third threshold;
- readings are taken by the chemical sensor while the heater is activated in response to the detection of a recharge process, wherein a deviation is determined between a current sensor reading and one or more of previous sensor readings, and wherein the heater is deactivated if the deviation is below a third threshold;
- the readings are taken periodically.

According to a further aspect of the present invention, a computer-readable storage medium is provided having stored thereon instructions for implementing a method according to any one of the previous embodiments when being executed on a control unit.

Other advantageous embodiments are listed in the dependent claims as well as in the description below.

The described embodiments similarly pertain to the apparatus, the method and the computer program element. Synergetic effects may arise from different combinations of the embodiments although they might not be described in detail.

BRIEF DESCRIPTION OF THE DRAWINGS

Embodiments and further aspects, features and advantages of the present invention can also be derived from the examples of embodiments to be described hereinafter and are explained with reference to the drawings. In the drawings the figures illustrate in FIG. 1 a mobile phone according to an embodiment of the present invention, FIG. 2 a top view on a sensor chip according to an embodiment of the present invention, FIG. 3 a cut through an individual sensor cell of the sensor chip of FIG. 2, FIG. 4 a block diagram of a portable electronic device according to an embodiment of the present invention, and FIG. 5 a flow chart representing a method for operating a portable electronic device according to an embodiment of the present invention.

DETAILED DESCRIPTION OF EMBODIMENTS

Figure 1:
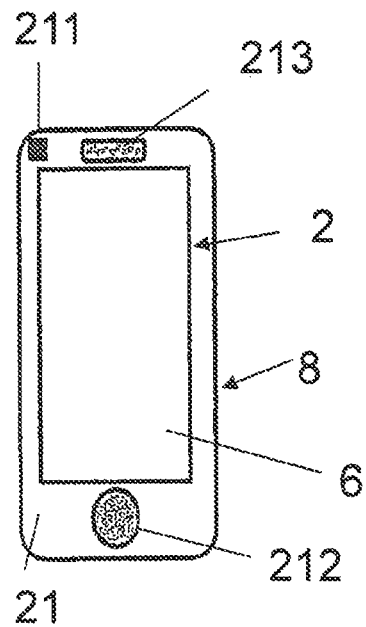

It is first pointed at general aspects of embodiments of the present invention.

A portable electronic device according to an embodiment of the present invention comprises a rechargeable energy storage, a chemical sensor comprising a sensitive layer and a heater for heating the sensitive layer, and a control unit for activating the heater subject to a detection of a recharge process for recharging the energy storage. In such portable electronic device, an impact of an offset drift of the chemical sensor on a measurement result may at least in some instances be reduced.

Chemical sensors that may be operated at elevated temperatures may suffer from an offset drift when the sensor is not operated, i.e. especially when the heater is not activated for a long time, e.g. for the reason of adsorption of water into the sensitive layer. It was found, that this drift may be reversible and an existing drift can be compensated by activating the heater again and by heating the sensitive layer for a sufficient period of time. However, in case such chemical sensor being arranged in a portable electronic device such as a smartphone or a tablet computer, maintaining the heater active for the sufficient period of time may, for example, require several 10 mW hrs of energy which energy may not be available due to a low energy level of the energy storage or due to an allocation of available energy to consumers in the portable electronic device other than the heater of the chemical sensor.

Hence, it was found by the applicant that a process of recharging the rechargeable energy storage, which may be a rechargeable battery in one embodiment, may be an ideal point in time to activate the heater for the above purpose. In general, heating the subject heater not for the purpose of measuring but for the purpose of out-gassing the sensitive layer for reducing a potential offset drift is also denoted as "reconditioning" of the chemical sensor or its sensitive layer in the following. Accordingly, the present idea refers to a reconditioning by activating the heater during the portable electronic device being recharged. In one embodiment, it is solely the detection of a recharge process triggering an activation of the heater. In such embodiment, the heater may be activated in response and/or as soon as a recharge process is detected. In addition, the heater may not be deactivated as long as the recharge process is active. By terminating the recharge process, the reconditioning may be terminated, too. In such scenario, the reconditioning is in synchronization with a recharging of the portable electronic device. In this respect, the recharge process of the portable electronic device may in a first embodiment include only the time in which the energy storage effectively is recharged, i.e. from the beginning of its recharge until the energy storage has reached its maximum charge state. In a different embodiment, the recharge process may cover a period from connecting the portable electronic device to a main supply, or generally an external power supply, until the portable electronic device is disconnected from such power supply irrespective if the energy storage has reached its maximum charge state at a point in time earlier than the portable electronic device is disconnected from the power supply. It is subject to the interpretation of a recharge period and subject to the availability of sensors which ones of the above alternatives may be applied. Preferably, in the first alternative, a sensor may monitor a capacity of the energy storage, while in the second alternative a sensor may monitor an electrical or mechanical connection to an external power supply.

However, the detection of a recharging state or process of the portable electronic device may not be the exclusive condition for activating the heater for reconditioning purposes. There may, in various embodiments, additional criteria be fulfilled in order to have the heater activated as will be explained later on.

The reconditioning of the portable electronic device includes activating the heater. Activating the heater may include turning the heater on, or may include increasing a heating power of the heater from a first heating level to a second, higher heating level. Accordingly, deactivating the heater may include turning off the heater or may include reducing the heating power from a second heating level to a first, lower heating level. Typically, the second higher heating level may be identical to a heating level applied during a sensor measurement.

The chemical sensor preferably comprises a layer that is sensitive to one or more analytes a presence of which shall be detected in a gas supplied to the chemical sensor. There may be a single sensitive layer made from a uniform material for interacting with the one or more analytes. Or there may be multiple sensitive layers made from different materials, for example, for interacting with different analytes. The chemical sensor performs a detection of chemical substances or compounds which are also denoted as analytes contained in a gas, or possibly in a fluid. Analytes may be, for example, CO2, NOX, ethanol, CO, ozone, ammonia, formaldehyde, or xylene without limitation.

Specifically, the sensitive layer may contain a metal-oxide material, and in particular a semiconducting metal oxide material. Such metal oxide material may include one or more of tin oxide, zinc oxide, titanium oxide, tungsten oxide, indium oxide and gallium oxide. Such metal oxides may be used for the detection of analytes such as VOCs, carbon monoxide, nitrogen dioxide, methane, ammonia or hydrogen sulphide.

Metal-oxide sensors are based on the concept that gaseous analytes interact with the metal oxide layer at elevated temperatures of the sensitive layer in the range of more than 100° Celsius, and specifically between 250° C. and 350° Celsius. As a result of the catalytic reaction, the conductivity of the sensitive layer may change which change can be measured. Hence, such chemical sensors are also denoted as high temperature chemoresistors for the reason that a chemical property of the analyte is converted into an electrical resistance at high temperatures of the sensitive layer.

Summarizing, the chemical sensor may in one embodiment comprise at least one sensor material, e.g. in form of a layer, an analyte may interact with and as such modify an electrical property of the sensor material such as its electrical conductance. Then, the electrical property of a combination of the analyte and the sensor material is measured and allows a conclusion as to the analyte, such as by way of comparison to a property of the sensor material measured without the presence of the analyte. It is noted that for the different analytes—which may be different chemical elements or chemical compounds—it is not required to always measure the same property per analyte. Different properties may be measured for different analytes.

Specifically, the chemical sensor may be a gas sensor for detecting one or more substances in a gas, and specifically in the air surrounding the portable electronic device. Hence, in a sample application it may be of interest to identify if such air may contain analytes the chemical sensor is prone to. Specific applications may include the detection of toxic gases, the detection of ethanol in a users breath, or the detection of other substances.

The chemical sensor preferably is arranged inside a housing of the portable electronic device. An opening may be provided in the housing for exposing the chemical sensor to a fluid to be analyzed.

Hence, any portable electronic device such as a mobile phone, and in particular a smart phone, a handheld computer, an electronic reader, a tablet computer, a game controller, a pointing device, a photo or a video camera, or a computer peripheral—which listing is not limited—may in addition to its original function provide chemical information as to its environment. The user may learn about chemical substances and compositions present in the devices surroundings, and may use, transmit or else further analyse such information. For the reason that such portable electronic device typically includes interfaces to a remote infrastructure, such information may be transmitted elsewhere and used elsewhere. In an alternative, the user himself/herself may benefit from the information provided by the chemical sensor in that actions can be taken in response to detected analytes, including but not limited to analytes representing toxic substances. Such portable electronic device as a result may primarily be designed for computing and/or telecommunication and/or other tasks in the IT arena, and now may be enhanced by the function of providing chemical information as to its environment.

In case the chemical sensor is sensitive of multiple different analytes the chemical sensor may be embodied as a sensor array. In such sensor array, each sensor cell may provide a sensor material, e.g. in form of a layer which is also denoted as sensitive layer, an analyte may interact with. In response to the interaction an electrical property of the sensor material such as its electrical conductance, may change which principle preferably is applied in metal oxide chemical sensors. In such scenario, the sensor array may comprise a single heater for all sensor cells, or may comprise multiple heaters, wherein each heater may be assigned for heating a group of sensor cells or an individual sensor cell, or the corresponding sensitive layer respectively. In case of multiple heaters, preferably all heaters are activated during reconditioning.

In another embodiment, the chemical sensor may comprise a single sensor cell, e.g. with a single layer, which however, may be sensitive to multiple different analytes under different operating conditions. For example, the sensor cell may mainly be sensitive to a first analyte x when being heated to a first temperature tx, and may mainly be sensitive to a second analyte y when being heated to a second temperature ty which is different from the first temperature tx. In another variant, a sensor array may comprise multiple sensor cells wherein at least one of the multiple sensor cells—and in another variant preferably all of the multiple sensor cells—is designed such that such cell/s may mainly be sensitive to different analytes under different operating conditions such as under different temperatures. In such specific embodiment, each of such cell/s may be provided with an individual heater. For reconditioning, it is preferred that all heating means available are activated.

In another embodiment, there may be at least one additional sensor provided in combination with the chemical sensor, such as a humidity sensor and/or a temperature sensor. These sensor/s may help in compensating temperature induced and/or humidity induced signal variations in a signal of the chemical sensor. Preferably the temperature sensor and/or the humidity sensor may be arranged in proximity to the chemical sensor, for example in the same opening.

According to another embodiment of the present invention, a method is provided for operating a portable electronic device. A recharge process for recharging a rechargeable energy storage of the portable electronic device is detected, and a heater is activated for heating a sensitive layer of a chemical sensor contained in the portable electronic device subject to the detection of the recharge process.

In a preferred embodiment, the heater is activated subject to the detection of the recharge process and subject to a period in time elapsed since the last time the heater has been activated in response to a recharge process. In another preferred embodiment, the heater is activated in response to the detection of the recharge process if the period in time elapsed since the last time the heater has been activated in response to a recharge process exceeds a first threshold. In these variants, activating the heater is prevented in case a period in time between two recharge events is that small, that a water diffusion process into the sensitive layer is not likely to occur during this period in time. The time between two recharge events after which a new reconditioning is desired to be applied is defined by the first threshold. The reference point in time, i.e. the time since the last time the heater has been activated in response to a recharge process shall not only include the exact point in time of activating the heater but shall include the event of the previous heating as such, be it its deactivating time, be it an average time, or any other specific point in time in connecting with the previous reconditioning event.

In another embodiment, the heater is activated subject to the detection of the recharge process and subject to a request for activating the heater. In a preferred embodiment, the heater is activated in response to the detection of the recharge process if a request for activating the heater is pending. In these embodiments, a user may indicate a necessity for reconditioning the chemical sensor, e.g. by pressing a key or touchkey for requesting a reconditioning at the next recharging of the portable electronic device. Hence such request may be pending and may trigger the reconditioning as soon as a recharge of the portable electronic device is initiated. Alternatively, a reconditioning request may trigger the reconditioning when issued during a recharge of the energy storage. Such request may also be issued by the device itself instead of the user, evoked, for example, by means of a timer.

According to another embodiment, the heater is activated subject to the detection of the recharge process and subject to a period in time elapsed since the last time the heater has been activated for conducting a measurement. In a preferred embodiment, the heater is activated in response to the detection of the recharge process if the period in time elapsed since the last time the heater has been activated for conducting a measurement exceeds a second threshold. These embodiments take into account that also during regular measurements the heater is activated and contributes to the outgassing of the chemical sensor. Hence, it may not be needed to recondition even if the previous recharge occurred a long time ago as long as one or more measurements were taken in between. The period in time which is considered to be sufficient between the last measurement and a current recharge is defined by the second threshold.

In another embodiment, the heater is activated subject to the detection of the recharge process and subject to a signal of a sensor. In a first embodiment, the sensor may be a sensor for sensing a different measure than the chemical sensor. In a second embodiment, the sensor may be a sensor arranged in a sensor package different to the sensor package the chemical sensor is arranged in. In a third embodiment, the sensor may be the chemical sensor or at least a part of the chemical sensor such as a cell of the chemical sensor embodied as an array of sensor cells. In another embodiment, the heater may be activated subject to signals of multiple sensors arranged in/at the portable electronic device. Specifically, a reconditioning heating may be triggered in case the recharge process is detected and the integrated signal of such sensor has exceeded an assigned threshold.

Such sensor may preferably be a sensor for sensing a humidity of the air/gas in the environment of the portable electronic device, wherein the humidity sensor may preferably be arranged in the portable electronic device. Under the assumption that at least a portion of the offset drift of the chemical sensor is caused by the adsorption of water into the sensitive layer of the chemical sensor, the humidity sensor may provide support in estimating at which point in time a reconditioning heating of the sensitive layer of the chemical sensor may be required. Specifically, a signal of the humidity sensor being integrated over time may be used to trigger or release the reconditioning heating since the integrated humidity reflects a dosage of humidity the chemical sensor was exposed to over time. Specifically, a reconditioning heating may be triggered in case the recharge process is detected and either the integrated humidity has exceeded an assigned threshold in the past or is doing so during the recharge of the portable electronic device. The integration of the humidity sensor signal may be started at one of the most previous heating for taking a reading and the most previous heating in response to a recharge process. Specifically, the termination of these events may be taken as a trigger to start the integration of the humidity sensor signal.

In another embodiment, readings, and preferably periodical readings are taken by the chemical sensor while the heater is activated in response to the detection of a recharge process. A deviation is determined between a current sensor reading and one or more of previous sensor readings. The heater is deactivated if the deviation is below a third threshold. By such activity the progress of outgassing is monitored. The better the chemical sensor is reconditioned, the less deviations are between subsequent measuring results. Hence, a deviation between two measurement results during the reconditioning may be taken as an indicator when to stop heating, i.e. when to deactivate the heater or when to reduce the power of the heater.

Same or similar elements are referred to by the same reference numerals across all Figures.

FIG. 1 illustrates a mobile phone 8 according to an embodiment of the present invention. Apart from a standard microphone as an input device which microphone is arranged in an opening 212 of a front wall 21 of a housing 2—which microphone may also be arranged in an opening of a side wall of the mobile phone 8, a chemical sensor is arranged in another opening 211 of the front wall 21, which opening 211 is arranged in proximity to yet another opening 213 for a standard speaker of the mobile phone 8. The chemical sensor may be used for detecting the presence of a gas or an odour in an environment of the mobile phone 8.

Figure 2:
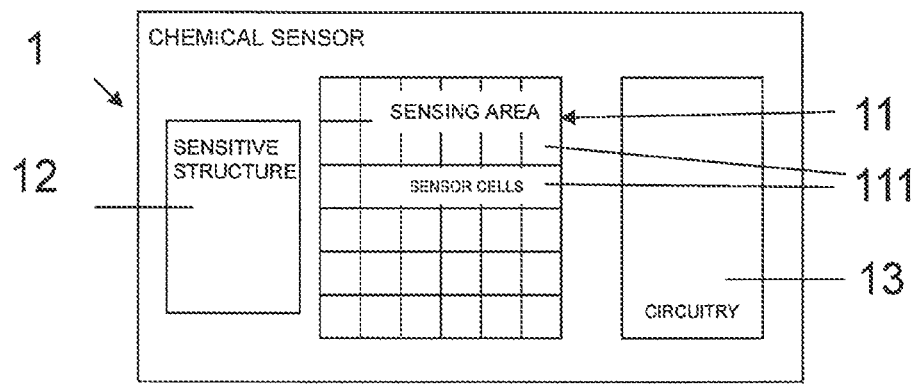

FIG. 2 illustrates a top view on a chemical sensor 1 represented by a sensor chip such as may be used, for example, in the mobile phone 8 of FIG. 1. The chemical sensor 1 comprises a chemical sensing area 11 which takes the shape of a sensor array comprising multiple sensor cells 111, in the present example, thirty six sensor cells 111. In addition a humidity and/or temperature sensitive structure 12 is arranged next to the chemical sensor array, and electronic circuitry 13 is integrated into the chemical sensor chip, too.

Figure 3:
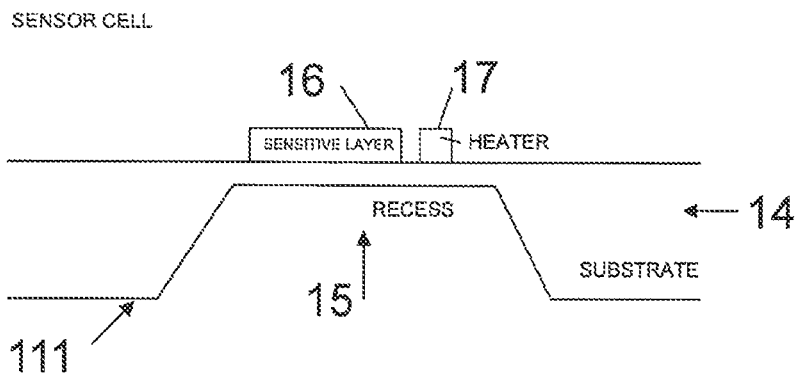

FIG. 3 illustrates a cut through a schematic individual sensor cell 111 in which a recess 15 is manufactured into a substrate 14 of the sensor chip. On top of a resulting thin membrane a sensitive layer 16 is arranged, and a heater 17, preferably a resistive heater 17, is arranged in or on top of the membrane. The membrane is also denoted as micro-hotplate for the reason that such membrane to a large extent constitutes a thermally insulating structure. Hence, any heat generation by the heater 17 affects the sensitive layer 16 as desired but does not leak into the bulk. The sensitive layer 16 preferably is made from a metal oxide material such as tin oxide. The sensitive layer 16 is heated by the heater 17 prior to taking a sensor reading, and preferably during taking a sensor reading for elevating a temperature of the sensitive layer 16 to a temperature sufficient for having a catalytic reaction between the analyte/s and the sensitive layer 16 to take place at a sufficient rate and as a result, for example, for having an electrical conductivity of the sensitive layer 16 modified. Such operating temperatures may vary subject to the material used from 100° degrees Celsius to 450° degrees Celsius. The micro-hotplate, preferably fabricated in MEMS technology, enables to achieve these temperatures in the sensing area without excessive power dissipation, since only a few 10 mW of electrical power is required for heating. While such power levels may be prohibitive for continuous mode measurements in mobile applications, single shot measurements, whereby the sensitive layer is powered up for a short time, e.g. in the order of 1 minute—and a single or a few measurement readings are taken, are possible.

The heater 17 may be used for both, heating the sensitive layer 16 prior to and/or during taking a sensor reading, and for heating the sensitive layer 16 for reconditioning purposes. However, in an alternative embodiment, there may a first heater be dedicated to the sensor reading and a second heater be dedicated to the reconditioning. For illustration purposes, other elements such as electrical contacts and leads for the heater 17 and the sensitive layer 16 etc. are not shown in FIG. 3.

Figure 4:
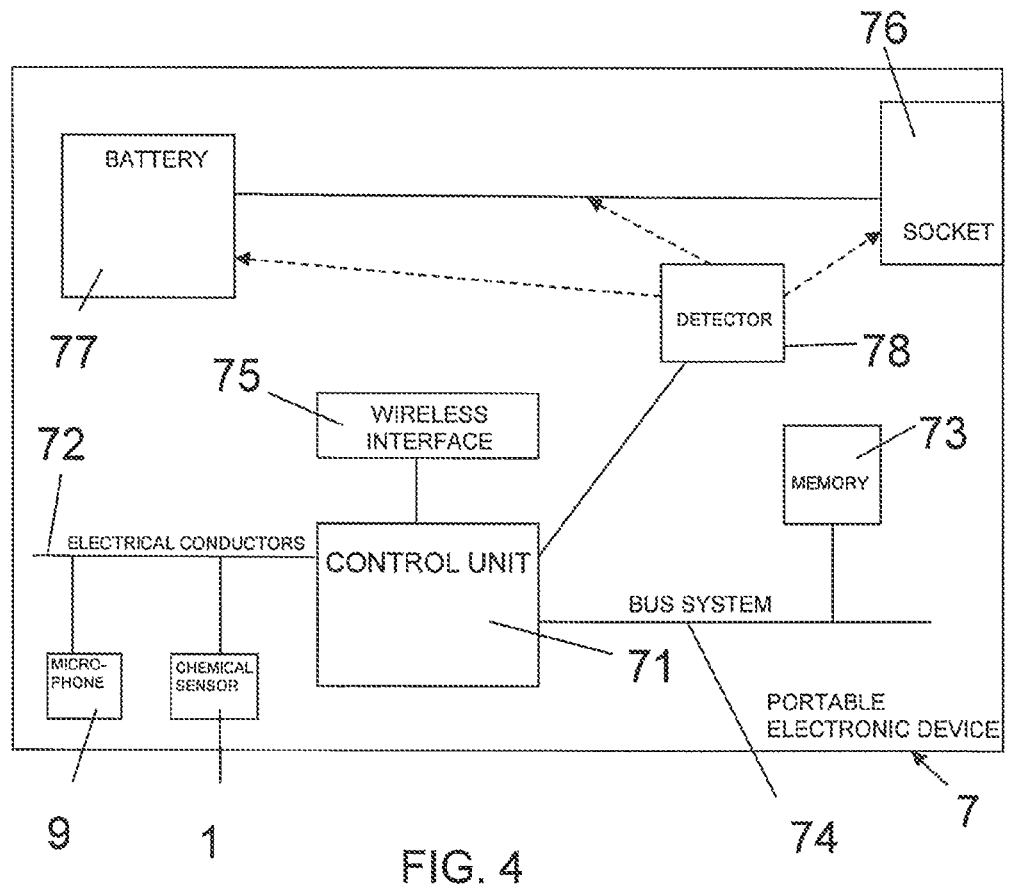

FIG. 4 shows a schematic hardware oriented block diagram of a portable electronic device 7. Here, a control unit 71 in form of a microprocessor is connected via electrical conductors 72 to multiple sensors including the chemical sensor 1, and to a microphone 9. A routine for analyzing the signals supplied by the chemical sensor 1 may be executed in the control unit 71, which routine is stored in a memory 73 connected to the microprocessor 71 via a bus system 74. A wireless interface 75 is connected to the microprocessor 71, too.

A socket 76 for receiving a charging cable is connected to a rechargeable battery 77. Whenever a charging cable is plugged into the socket 76 and the portable electronic device 7 is thereby connected to a main supply the rechargeable battery 77 will be charged. A detector 78 is provided for detecting a recharge process. As indicated by the dotted line arrows, the detector 78 may, for example, detect if a charging cable is plugged into the socket 76 and as such detect a mechanical plug. In another variant, the detector 78 may detect if current is supplied form the socket 76 to the rechargeable battery 77. In another variant, the detector 78 may monitor a capacity, or more generally a charge state of the rechargeable battery 77 and derive from this state if the rechargeable battery 77 currently is charged. Any such indicator as to the detection of a charging process will be submitted to the control unit 71.

Figure 5:
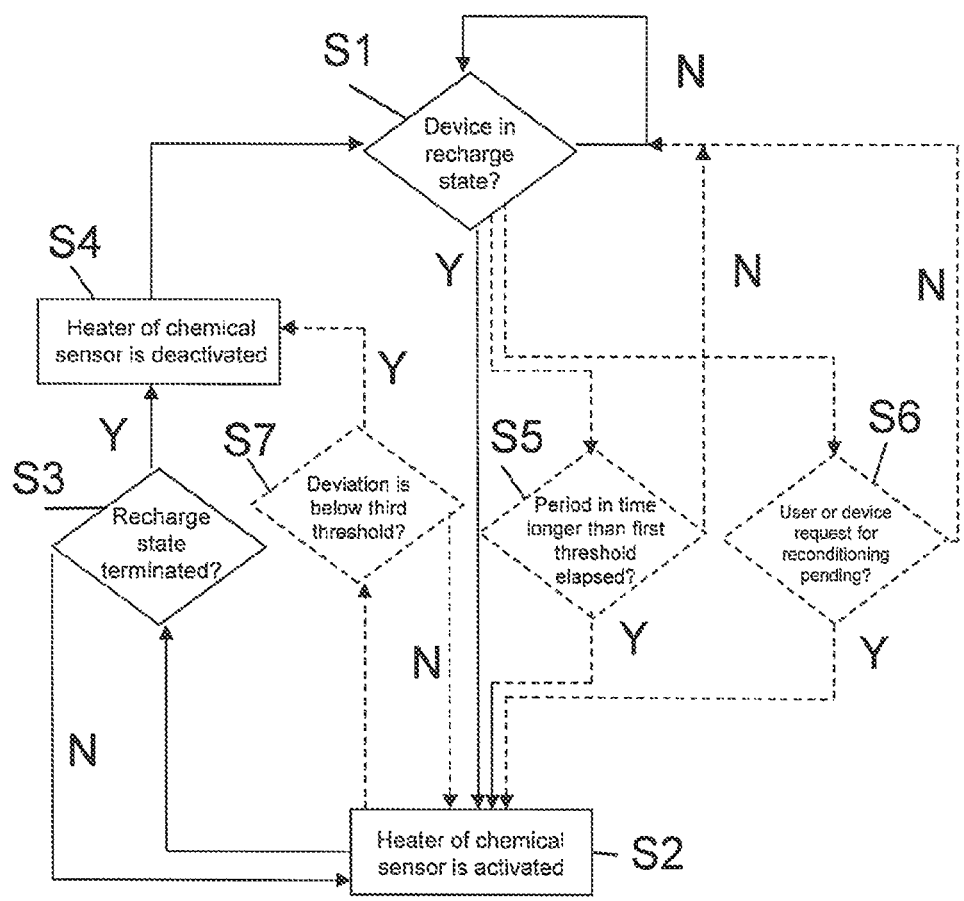

FIG. 5 illustrates a flow chart representing a method according to an embodiment of the present invention. In step S1, it is monitored if the portable electronic device is in a recharge state. If not (N) the monitoring continues. If yes (Y), in step S2 a heater of a chemical sensor of the portable electronic device is activated. In step S3, it is verified if the recharge process has terminated yet. If not (N) the heater continues heating in step S2. If yes (Y) the heater is deactivated in step S4, and optionally a date and time stamp is recorded for the event of deactivating the heater. In step S1 is verified if a new recharge process is initiated.

The dashed lines indicate variants of the above method. In case, a recharge state was detected in step S1 (Y), it is verified in step S5 if a period in time longer than a first threshold has elapsed since the most previous recharge. Only if such period in time has exceeded the first threshold (Y) the heater is activated in step S2. Otherwise (N), the heater will not be activated and no reconditioning will be performed at this point in time. Instead of the period in time since the most previous reconditioning, a period in time since the most previous measurement may be applied, too. In another variant, if a recharge state was detected in step S1 (Y), it is verified in step S6 if a user or device request for reconditioning is pending. Only if such request is pending the heater is activated in step S2. Otherwise (N), the heater will not be activated and no reconditioning will be performed at this point in time (N).

There may be an alternative to the present de-activation for the heater applied: Instead of waiting for an end of the recharge which may be detected, for example, by the very same detector 78, sensor readings may be taken during the reconditioning in step S2. In step S7 the present reading may be compared to the most previous reading and a deviation may be compared to a third threshold. In case the deviation is below the third threshold (Y) the heater is deactivated in step S4. In case the deviation is above the third threshold (N), the heater continues heating.

While there are shown and described presently preferred embodiments of the invention, it is to be distinctly understood that the invention is not limited thereto but may be otherwise variously embodied and practised within the scope of the following claims.

The invention claimed is:

1. Method for operating a portable electronic device, comprising
    detecting a recharge process for recharging a rechargeable energy storage of the portable electronic device, and
    activating a heater for heating a sensitive layer of a chemical sensor contained in the portable electronic device,
    wherein the heater is activated subject to the detection of the recharge process and subject to a period of time elapsed since the last time the heater has been activated in response to a recharge process.

2. Method according to claim 1,
    wherein the heater is deactivated in response to a termination of the recharge process.

3. Method according to claim 1,
    wherein the heater is activated in response to the detection of the recharge process if the period of time elapsed since the last time the heater has been activated in response to a recharge process exceeds a first threshold.

4. Method according to claim 1,
    wherein readings are taken by the chemical sensor while the heater is activated in response to the detection of a recharge process,
    wherein a deviation is determined between a current sensor reading and one or more of previous sensor readings, and
    wherein the heater is deactivated if the deviation is below a first threshold.

5. Method according to claim 4,
    wherein the readings are taken periodically.

6. Computer-readable storage medium having stored thereon instructions for implementing a method according to claim 1 when being executed on a control unit.

7. Method for operating a portable electronic device, comprising
    detecting a recharge process for recharging a rechargeable energy storage of the portable electronic device, and
    activating a heater for heating a sensitive layer of a chemical sensor contained in the portable electronic device,
    wherein the heater is activated subject to the detection of the recharge process and subject to a period of time elapsed since the last time the heater has been activated for conducting a measurement.

8. Method according to claim 7,
    wherein the heater is activated in response to the detection of the recharge process if the period of time elapsed since the last time the heater has been activated for conducting a measurement exceeds a first threshold.

9. Method according to claim 7,
    wherein the heater is deactivated in response to a termination of the recharge process.

10. Method according to claim 7,
    wherein readings are taken by the chemical sensor while the heater is activated in response to the detection of a recharge process,
    wherein a deviation is determined between a current sensor reading and one or more of previous sensor readings, and
    wherein the heater is deactivated if the deviation is below a first threshold.

11. Method according to claim 10,
    wherein the readings are taken periodically.

* * * * *